United States Patent
Fraites et al.

(10) Patent No.: US 10,864,316 B2
(45) Date of Patent: Dec. 15, 2020

(54) NEEDLE PACKAGING

(71) Applicant: Becton, Dickinson and Company, Franklin Lakes, NJ (US)

(72) Inventors: Thomas Fraites, Ringwood, NJ (US); Adam Kristopher Brakoniecki, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/258,941

(22) Filed: Jan. 28, 2019

(65) Prior Publication Data

US 2020/0237999 A1 Jul. 30, 2020

(51) Int. Cl.
*A61M 5/00* (2006.01)
*B65D 25/04* (2006.01)

(52) U.S. Cl.
CPC ............ *A61M 5/008* (2013.01); *A61M 5/002* (2013.01); *B65D 25/04* (2013.01)

(58) Field of Classification Search
CPC .... A61M 5/002; A61M 5/008; A61M 5/3205; A61M 5/3129; A61M 2005/3254; B65D 1/36; B65D 25/04; B65D 25/108; B65D 85/42; B65D 2101/00
USPC .... 206/365–366, 443, 562, 210, 438, 45.23, 206/486, 564, 571; D24/130, 227, 230
See application file for complete search history.

(56) References Cited

U.S. PATENT DOCUMENTS

| 2,435,994 A * | 2/1948 | Zukerman | A61M 5/001 206/366 |
| 2,523,877 A * | 9/1950 | Pestolesi | A61M 5/008 206/366 |
| 3,853,217 A | 12/1974 | Scordato et al. | |
| 3,876,067 A * | 4/1975 | Schwarz | A61M 5/001 206/205 |
| 3,937,322 A | 2/1976 | Cohen | |
| 4,166,533 A | 9/1979 | Maitland | |
| 4,671,408 A * | 6/1987 | Raines | A61M 5/002 206/1.5 |
| 4,729,208 A * | 3/1988 | Galy | A61M 5/00 53/127 |
| 4,919,264 A * | 4/1990 | Shinall | A61M 5/3205 206/210 |
| 5,004,103 A * | 4/1991 | Connors | B25H 3/02 206/372 |
| 5,190,169 A * | 3/1993 | Sincock | A61M 5/3213 206/366 |

(Continued)

FOREIGN PATENT DOCUMENTS

| CN | 201065242 Y | 5/2008 |
| EP | 2944583 A1 | 11/2015 |

OTHER PUBLICATIONS

PCT International Search Report in PCT/US2020/015142 dated May 8, 2009, 17 pages.

*Primary Examiner* — Chun Hoi Cheung
*Assistant Examiner* — Brijesh V. Patel
(74) *Attorney, Agent, or Firm* — Servilla Whitney LLC

(57) ABSTRACT

Packages of sterile needles are described herein. Such packages may include a container, a tray having a plurality of receiving apertures that are sized and shaped to receive a needle hub or a needle shield, a plurality of needles disposed within the plurality of receiving apertures; and a lid being supported by the container. The lid and container form an enclosure for the plurality of needles.

4 Claims, 8 Drawing Sheets

(56) References Cited

U.S. PATENT DOCUMENTS

| | | | | |
|---|---|---|---|---|
| 5,285,896 A * | 2/1994 | Salatka | A61M 5/3205 | 206/366 |
| 5,366,088 A * | 11/1994 | Hill | B01L 9/543 | 206/443 |
| 5,372,252 A * | 12/1994 | Alexander | A61M 5/001 | 206/210 |
| 5,396,989 A * | 3/1995 | Hein | A61B 17/205 | 206/366 |
| 5,975,295 A * | 11/1999 | Diamond | A61M 5/008 | 206/366 |
| 6,019,225 A * | 2/2000 | Kalmakis | B01L 9/543 | 206/443 |
| 6,230,985 B1 * | 5/2001 | Wang | B05B 15/65 | 239/273 |
| 6,263,641 B1 * | 7/2001 | Odell | B65B 55/10 | 53/425 |
| 6,346,094 B2 * | 2/2002 | West | A61M 5/002 | 206/365 |
| 6,796,440 B2 * | 9/2004 | Wang | A47F 7/0028 | 211/183 |
| 7,665,491 B2 * | 2/2010 | Lampropoulos | A61B 50/33 | 141/311 A |
| 8,162,138 B2 * | 4/2012 | Bettenhausen | A61L 2/26 | 206/339 |
| 8,177,063 B1 | 5/2012 | Simm | | |
| 8,490,790 B2 * | 7/2013 | Cocheteux | A61M 5/008 | 206/364 |
| 8,827,075 B2 * | 9/2014 | Seiwell | A61M 5/008 | 206/366 |
| 8,875,880 B2 * | 11/2014 | Benczkowski | B25H 3/06 | 206/338 |
| D825,926 S * | 8/2018 | Lauber | D3/318 | |
| 2005/0109649 A1 * | 5/2005 | Natoli | B25H 3/003 | 206/372 |
| 2012/0061274 A1 * | 3/2012 | Tumminello | A61B 17/06128 | 206/438 |
| 2013/0062245 A1 * | 3/2013 | Folchini | A61M 5/002 | 206/571 |
| 2014/0014654 A1 * | 1/2014 | Gerner | A61M 5/008 | 220/23.83 |
| 2015/0122693 A1 * | 5/2015 | Deutschle | B65D 25/108 | 206/562 |
| 2016/0121042 A1 * | 5/2016 | Christensen | B65D 25/108 | 206/366 |
| 2016/0193427 A1 * | 7/2016 | Limaye | A61M 5/002 | 206/365 |
| 2018/0360178 A1 * | 12/2018 | Bungert | A45C 11/20 | |

* cited by examiner

NEEDLE PACKAGING

TECHNICAL FIELD

An aspect of the present disclosure relates generally to a sterile bulk packaging for needles and, more particularly, to a rack assembly for needles.

BACKGROUND

Hypodermic syringes and needles are widely used in the medical arts for administering medicaments and for drawing body fluid samples. Generally, hypodermic syringes include a removably attached needle that has a sharpened distal point for penetrating vial stoppers or a patient's skin. The needles are often disposable. The use of needles requires provisions intended to both protect health care workers from accidental needle sticks and to maintain the sterility and integrity of the needle prior to use. A variety of shielding mechanisms have also been developed which are intended to shield the needle before and after it has been used in order to reducing the risk of an accidental needle stick.

Thus, there is a need for a bulk sterile needle packaging that allows users to access a large quantity of needles, both shielded and unshielded, in a compact carrier in which the needles are both readily accessible to a technician or other person using the item and may be put in use without the necessity of a technician handling the item.

SUMMARY

One aspect of the present disclosure pertains a package of sterile needles including a container having a body including a bottom portion and a side portion connected to and extending from the bottom portion, a tray having a plurality of receiving apertures spaced apart, a plurality of needles disposed within the plurality of receiving apertures, and a lid being supported by said container. The receiving apertures are sized and shaped to receive a needle hub or a needle shield. The lid and container form an enclosure for the plurality of needles.

In one or more embodiments, the plurality of apertures may be in the shape of a cruciform, square, rectangle, or triangle.

In one or more embodiments, the package or container is sealed in a heat seal closure. In one or more embodiments, the body of the container includes one or more tortuous path closures. In one or more embodiments, the lid includes one or more tortuous path closures.

In one or more alternate embodiment, a friction enhancing material is disposed within the plurality of receiving apertures. The friction enhancing material may be rubber or silicone. In one or more alternate embodiment, a friction enhancing texture may be molded into the surface of the plurality of receiving apertures. The friction enhancing texture may be in the form of a knurl pattern or surface treatment on the surface of the plurality of receiving apertures.

DETAILED DESCRIPTION

Figure 1:
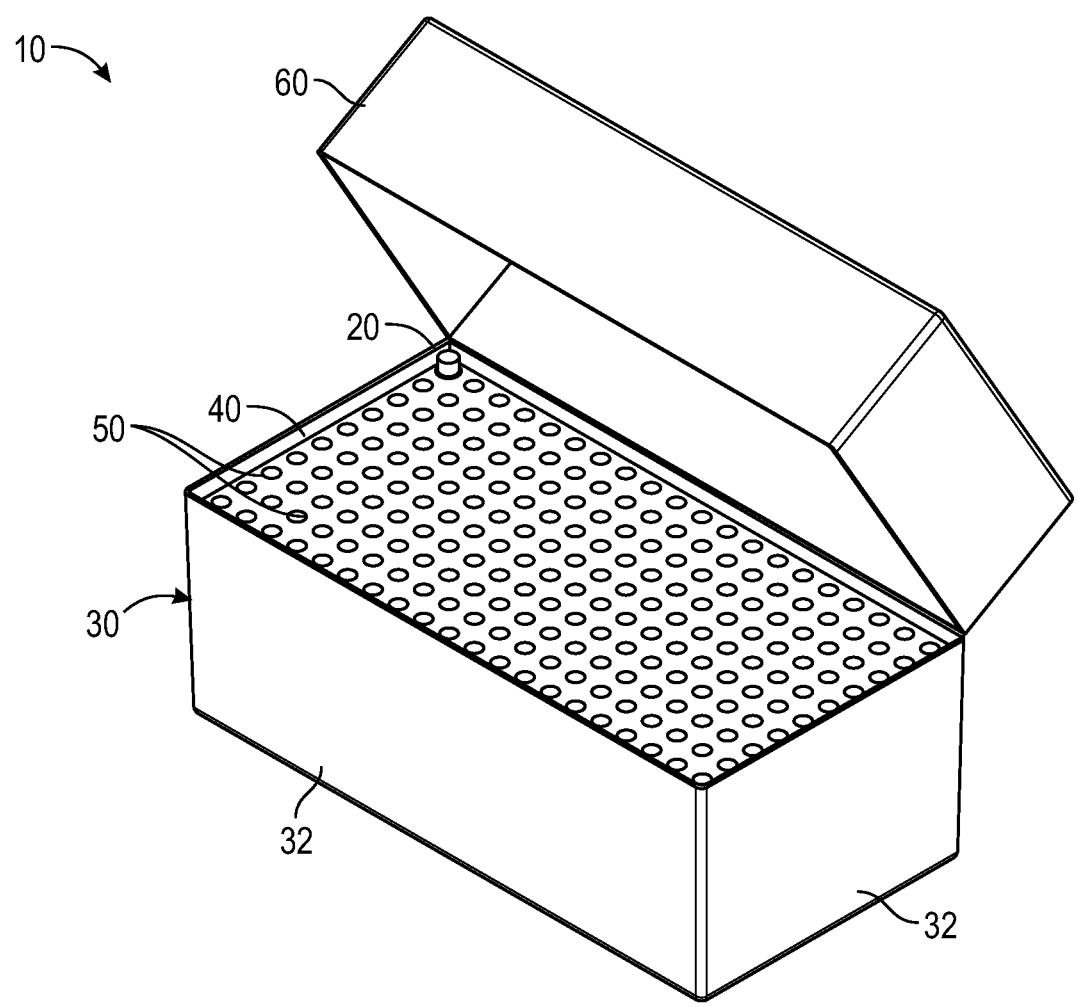
FIG. 1 illustrates a perspective view of a needle packaging with one representative needle illustrated according to a first embodiment.

Before describing several exemplary embodiments of the present disclosure, it is to be understood that the embodiments of the present disclosure are not limited to the details of construction or process steps set forth in the following description and drawings. The present disclosure is capable of other embodiments and of being practiced or carried out in various ways. Additionally, in the following, items which are substantially the same across the various embodiments are given the same reference numbers.

With respect to terms used in this disclosure, the following definitions are provided.

As used herein, the use of "a," "an," and "the" includes the singular and plural.

Reference to "syringe" includes syringes that are indicated for use with needles, nozzle, tubing, or for use in flush systems. The open end of the syringe may be fitted with a needle, nozzle, or tubing to help direct the flow of fluid into and out of the barrel.

As used herein, the terms "closure system" includes any material used to wrap or protect a good or product, such as a package or syringe. The closure system can be rigid or flexible.

As used herein, the term "microorganism" refers to a microbe or organism that is unicellular or lives in a colony of cellular organisms. Microorganisms are very diverse; they include, but are not limited to bacteria, fungi, archaea, and protozoans.

As used herein, the term "needle" refers to needle cannula, needle hub, needle shield, needle cannula attached to a needle hub and a needle cannula enclosed within a needle shield.

Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

As used herein, the term "sterilization" refers to a means of eliminating or killing microorganisms present on a surface, contained in a fluid or in a compound such as biological culture media in order to achieve asepsis or a sterile microbial environment. Sterilization can be achieved by applying heat, chemicals, irradiation/radiation, high pressure, filtration, or combinations thereof. Chemical sterilization includes sterilization with gases such as ethylene oxide, hydrogen peroxide gas, and ozone, liquids such as chlorine bleach, iodine, glutaraldehyde and formaldehyde, ortho-phthaladehyde (OPA), hydrogen peroxide, peracetic acid, sodium hydroxide, silver, and cobalt. Radiation sterilization involves the use of radiation such as electron beams (E-beam), x-rays, gamma rays, or subatomic particles.

As used herein, the term "tortuous path" refers to a long known principle established by Louis Pasteur. In experiments, Pasteur fashioned glass flasks with various neck shapes. Each flask contained an enclosed sterile media. The necks on some flasks allowed microorganisms to fall on the contained media, which then became contaminated as evidenced by bacterial growth. The media in flasks with S-curved necks, or in those flasks which presented a "tortuous path" for microorganisms, remained sterile. The microorganisms were stopped at the openings to the curved necks, as well as at the curves in the necks.

As used herein, the term "tortuous path ring" refers to a ring, circle, loop, band, sphere, etc. that creates a barrier between the contaminated exterior and the sterile interior region of the syringe assembly by creating an extended pathway with a plurality of interruptions that prevents the migration of microorganisms from the outside of the package into the tray.

As used herein, the term "irregularly shaped" refers to a cross-sectional shape that provides a surface or edge that is detrimental to free rotation about the cross-section.

The package of the present disclosure is intended for use with a needle device. A needle device may be removably coupled to a standard or specially configured needle shield or needle hub/syringe. An exemplary embodiment of a needle device may include a hub, a needle cannula having a proximal end attached to the hub and distal tip.

In one or more embodiments, the needle device may be connectable to a luer connection or other fluid connector via the hub. A needle cannula may be connected to hub. The needle cannula extends from the needle hub and extends to a distal tip. In one or more embodiments, needle cannula may have a sharpened or beveled distal tip. Needle cannula is disposed in the hub in a manner as would be well understood in the art. Hub may be configured to be removable or permanently attached to a syringe, or alternatively, hub may be integrally formed with a syringe. For example, the hub may include internal or external threads or other suitable coupling, latching, or locking features such as tabs, slots, projections, pressure/snap fits, and the like, for removably coupling the needle device to a syringe. The hub includes outwardly extending projections and is placed on a distal end of a syringe barrel by aligning the distal end of the barrel with a cavity in the hub so that the outward projections of the hub engage threads in a locking luer collar of the syringe barrel. Needle assembly is then rotated or screwed into the locking luer collar so that the needle assembly is held tightly on the distal end of the syringe barrel through interaction of the locking luer collar thread and the projections on the needle hub and a frictional interference fit between elongate tip on the barrel and cavity in the hub. Hub is in fluid communication with the needle cannula to permit fluid to pass between a syringe and the needle cannula. In one or more embodiments, the needle device may include a needle shield adapted to secure the tip of the needle within the shield before and after use of the needle. Therefore, embodiments of the present disclosure include a tray to house the needle hubs or needle shield having a keying or locking feature to hold the needle hubs and/or shields in place to ensure that the needle hub or needle shield does not rotate while the needle is being attached to a syringe. An advantage of the embodiments of the present disclosure over known packaging solutions is that the locking feature enables a positive engagement between the syringe and the needle hub or needle shield to allow for single-handed operation by the user.

Syringes and other medical devices having a luer fitting or connection are often assembled with needle hubs or luer fittings. Two common mechanisms used to connect the needle hubs to the syringes include the "luer lock" and "luer slip" mechanisms.

The luer lock mechanism generally includes a male conical fitting in co-axial relation with an internally threaded collar. A cooperating needle hubs or female luer lock fittings have external lugs for engaging the internally threaded collar of the male conical fitting, upon application of a twisting force or torque force to the needle hub. To complete attachment of the needle hub to the syringe, the twisting force must be continued until the external lugs can no longer be threaded into the internally treaded collar of the male conical fitting. To detach the needle hub from the syringe, a twisting force in the opposite direction must be applied to the needle hub. It has been observed that the male conical tip can break off during application of this twisting force and is lodged in the needle hub, rendering both the needle hub and syringe useless.

Cooperating needle hubs or female luer slip fittings have an internal surface which slides over the external surface of the male conical fitting. In one or more embodiments, the needles are used by pressing the tapered distal tip of a syringe into a tapered proximal opening of the needle to frictionally engage the syringe and needle to create a luer slip connection. The needle hub is attached to the male conical fitting in a friction fit relationship. To attach of the needle hub to the male conical fitting, the user must apply enough force with sliding the needle hub to create a fluid tight relationship between the needle hub and male conical fitting. Failure to securely connect the needle hub and medical device can result in "pop offs," where the unsecured needle hub detaches from the male conical fitting during use.

The luer lock mechanism generally includes a fluid storage container with a male fitting in co-axial relation with an internally threaded collar. A cooperating hub or female luer lock fittings have external lugs for engaging the internally threaded collar of the male conical fitting, upon application of a twisting force or torque force to the hub. In one or more embodiments, the needles are used by pressing the syringe into a tapered proximal opening of the needle and rotating the syringe to engage with the thread and for a luer lock connection.

The luer slip fitting generally includes a fluid storage container with a male fitting without a threaded collar.

In general, the present disclosure describes a package for a large quantity of sterile needles, the carrier including a tray having a plurality of spaced receiving apertures configured to releasably house one or more needles, often disposed of in an array the needles such that the needles project through the tray but are supported thereon by their receiving apertures. In one or more embodiments, the tray having a plurality of receiving apertures organizes a plurality of sterile needles such that the needles can be efficiently placed onto syringes. In one or more embodiments, the needles may be shielded with a needle shield. In one or more embodiments, the needles are attached to a needle hub and may be unshielded. In one or more embodiments, the tray walls may be tapered, sloped, curved or provided with a peripheral shoulder so that the trays may be stacked. When the trays are stacked one above another, each tray is supported by the shoulder of the wall of the tray below. One or more stacks of needle loaded trays may be placed in a container for shipment and distribution.

Figure 2:
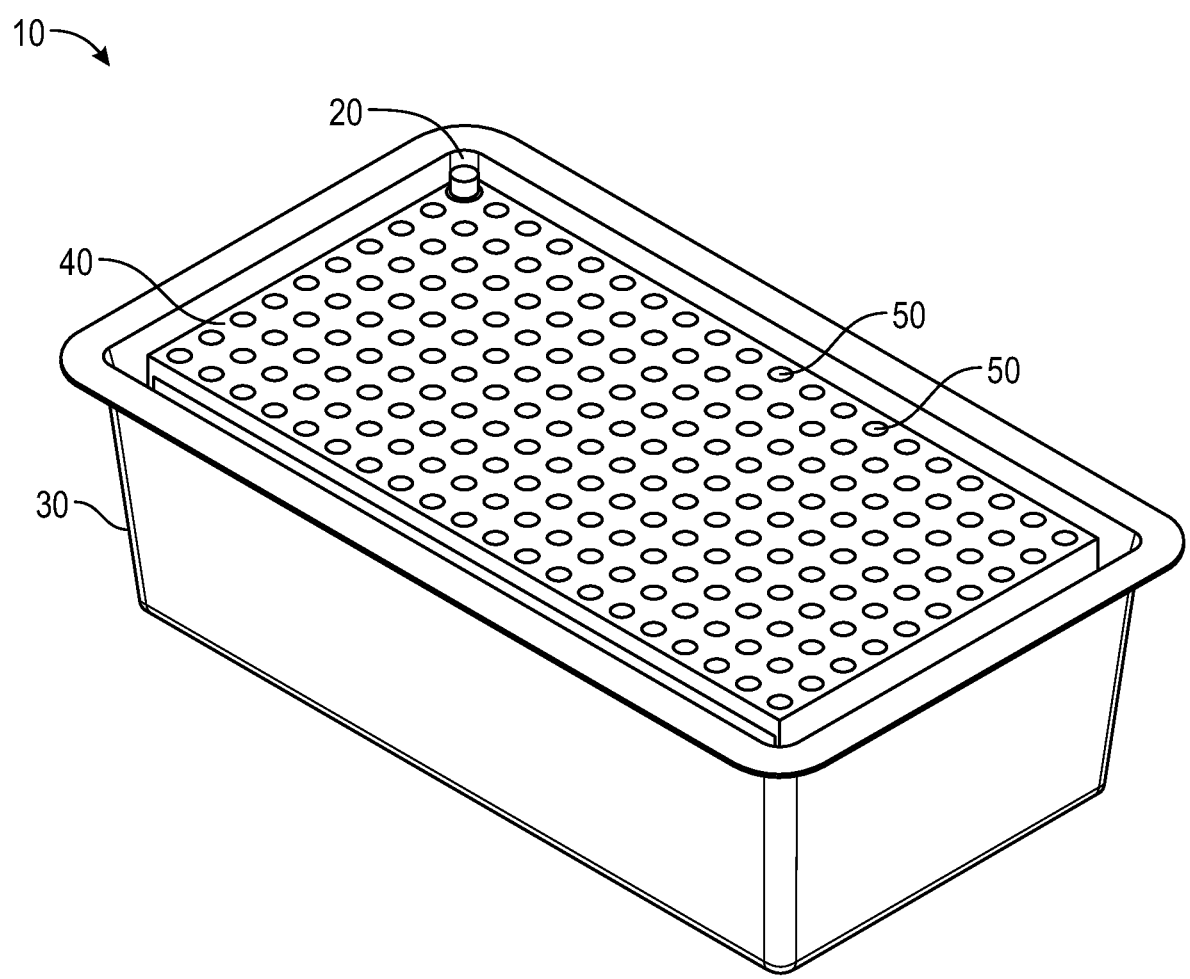
FIG. 2 illustrates a perspective view of a needle packaging of FIG. 1 without a lid.
Figure 3:
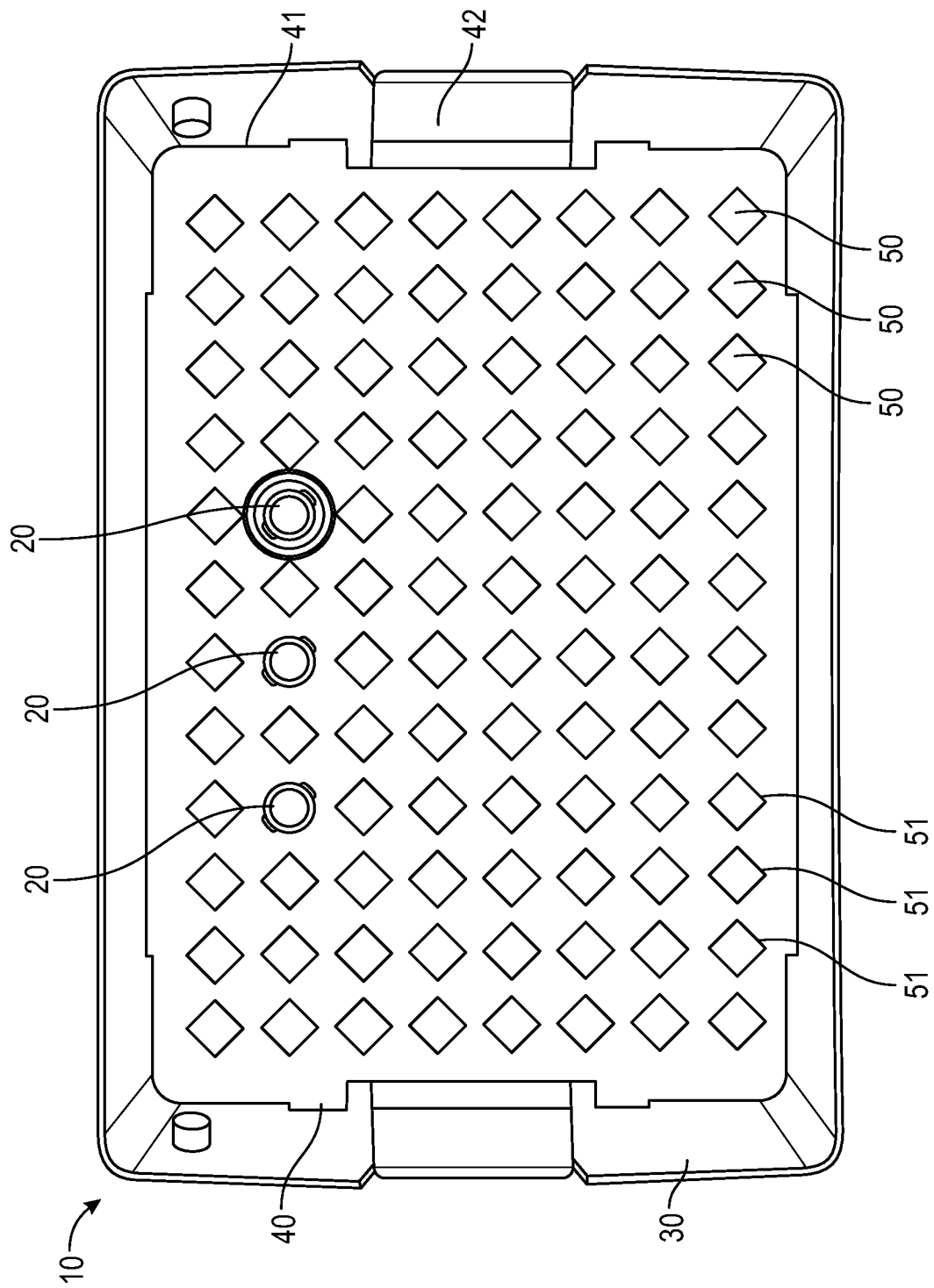
FIG. 3 illustrates a top view of a container and tray having a representative square-shaped locking feature for a needle hub or needle shield of the needle packaging with a few representative needles illustrated according to an embodiment.
Figure 4:
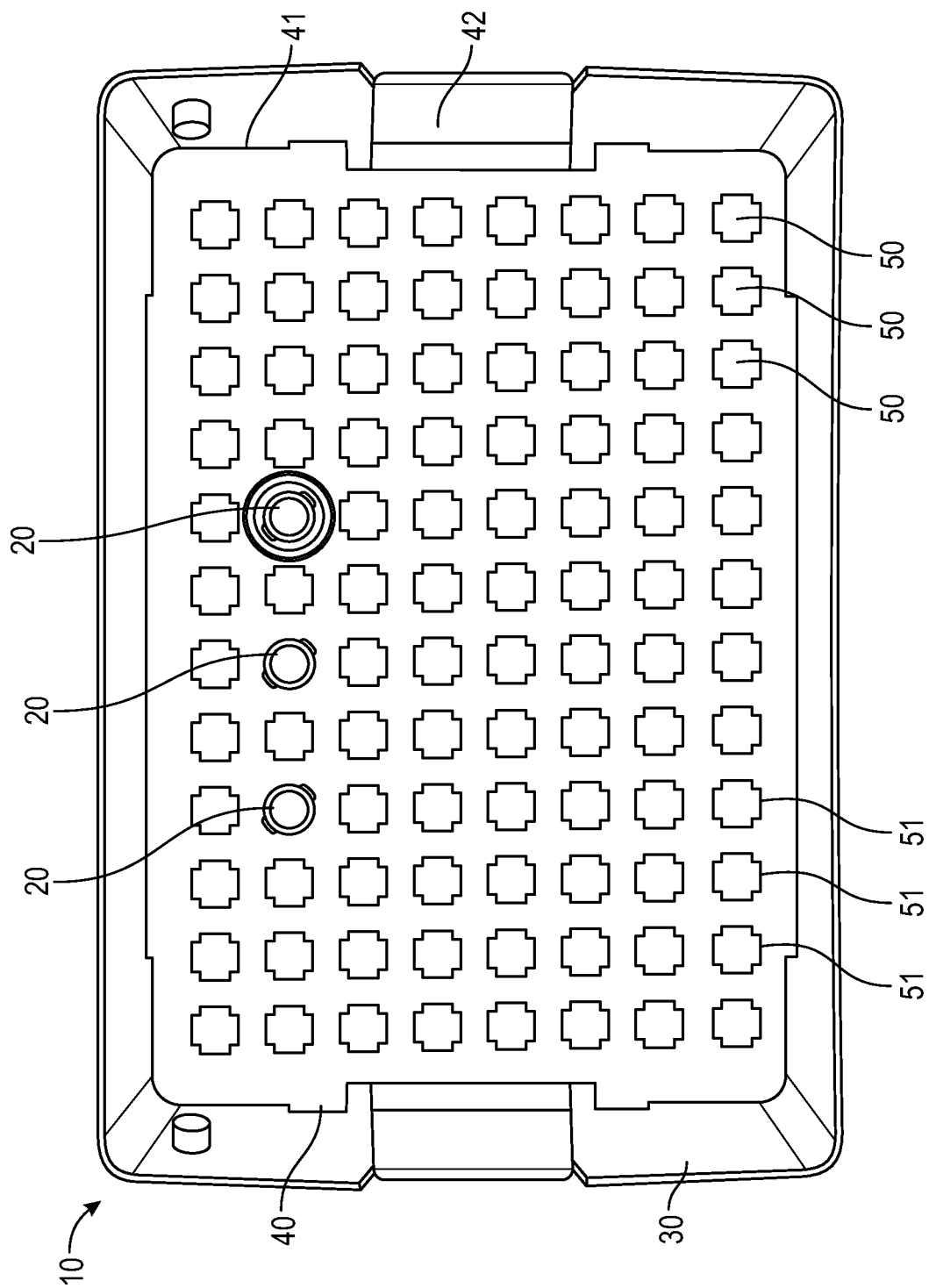
FIG. 4 illustrates a top view of a container and tray having a representative cruciform-shaped locking feature for a needle hub or needle shield of the needle packaging with a few representative needles illustrated according to an embodiment.

FIGS. 1 and 2 illustrate an exemplary package 10 of sterile needle hubs or needle shield 20 according to the present disclosure. The needle hubs or needle shield 20 are attached to or cover a needle cannula. Referring to FIGS. 1-3, a package 10 according to the present disclosure generally includes a plurality of sterile needles 20 having a container 30, a tray 40 having a plurality of receiving apertures 50 spaced apart such that the receiving apertures 50 are sized and shaped to receive a plurality of needles, needle hub or needle shield 20 disposed within the plurality of receiving apertures 50, and a lid being supported by the container 30. The lid 60 and container 30 form an enclosure for the plurality of needles 20.

One or more embodiments of the present disclosure include a container 30 having a lid 60. Lid 60 may include a hinge and/or a clasp configured to permanently or reversibly attach the lid to the container. As shown in FIG. 1, lid 60 may be attached hingedly to container 30 with the lid 60 being movable in a pivotal fashion to open and close. In one or more embodiments, the lid 60 is covered with a tamper-evident band.

As shown in FIGS. 1 and 2, container 30 has a bottom wall and four opposing side walls 32, all fixedly attached to one another and to providing an enclosure with a substantially box-like square or rectangular configuration and defining an interior cavity for the placement of one or more trays. In certain embodiments, container 30 comprises four side walls 32 arranged in a substantially rectangular shape and a bottom substantially coextensive with the four side walls. In some embodiments, the four sidewalls are coextensive and secured to a bottom thereby forming a open box-like configuration (e.g., a box with 4 sides, a bottom and no top).

In one or more embodiments, a sidewall 32 and/or a bottom of a container 30 is substantially rectangular in shape. A sidewall 32 comprises an interior surface and an exterior surface. In some embodiments, the container comprises two opposing long sidewalls and two opposing short sidewalls.

In one or more embodiments, any two sidewalls (e.g., a long sidewall and a short sidewall) are joined at a junction at an angle of about 90 degrees. In one or more embodiments, a junction comprises a curve and/or a corner. In one or more embodiments, a junction comprises a flange with a ridge and/or a lip configured to engage, support, retain and/or secure the tray. A ridge and/or a lip can be any suitable height, depth, width, or height.

In one or more embodiments, as shown in FIGS. 3-6, tray 40 includes a panel 41 with a plurality of receiving apertures 50, tray sidewalls, tray endwalls. In one or more embodiments, tray 40 may also include a tray flange 42. The plurality of receiving apertures 50 are spaced apart and adapted to retain the needle hub or needle shield therein. In one or more embodiments, the receiving apertures have a continuous side wall with an open top end and a bottom end which may be open or closed. The continuous side wall of the receiving aperture may be tapered. The depth of the receiving aperture is sufficient to hold a needle hub or needle shield such that the sidewall of a needle shield or sidewall of the unshielded needle hub will be supported by the sidewalls of the receiving apertures. Each receiving aperture is open at the top end of its continuous side wall adjacent to the opening in the top wall so as to receive the needle hub or needle shield which is inserted through the opening. The receiving apertures 50 thus isolate the needle hub or needle shield from one another in the tray 40. In one or more embodiments, the needle hub or needle shield is attached to the receiving apertures 50 in the tray 40 in a friction fit relationship. Needle hubs or needle shields are generally captured in each receiving aperture such that a smaller portion of the axial length of each needle hub or needle shield is disposed above and a larger portion of the axial length of each needle hub or needle shield is disposed below the tray 40. Contact of the sidewall of a needle shield or sidewall of the unshielded needle hub with the sidewall of the receiving aperture will prevent rotation of the needle hub or needle shield when the needle hub or needle shield is being connected with a syringe. Although rotation of the needle hub or needle shield is prevented when the needle hub or needle shield is being connected with a syringe, the needle is freely removable from the tray 40 by the user when desired. The receiving aperature is configured to receive one needle hub or needle shield per aperture. In some embodiments plate bores are arranged in a suitable array, non-limiting examples of which include an 8×12 array (as shown in FIG. 3-6) or 10×20 array (as shown in FIG. 1-2). In one more embodiments, the panel 41 is generally rectangular in shape (as shown in FIGS. 1-6). To remove the needle and syringe assembly from the tray 40, the user applies pressure in a vertically upward direction to remove the needle from the receiving aperature 50 of the tray 40. Thus, the user will not contaminate the needle before its use, nor be in danger of needle stick due to touching the tip of the needle.

In some embodiments a tray 40 comprises tray sidewalls that projects in a downward direction from the top surface of the panel. In some embodiments a tray flange 42 may extend from one or more of the tray sidewalls.

In some embodiments a tray 40 comprises a tab that projects in a coplanar direction with a tray sidewall. In some embodiments a tray flange or tab is used as a surface for gripping and sometimes for removing a tray 40 from a container 30.

In one or more embodiments, one or more trays 40 can be stacked one above another.

In one or more embodiments, the connection between the needle hub or needle shield 20 to the receiving aperture 50 of the tray 40 may also incorporate connection mechanism selected from an friction fit, interference fit, snap fit, locking means and combinations thereof.

The receiving aperature 50 of the tray 40 may be modified to prevent rotation of the needle hub or needle shield when the needle hub or needle shield is being connected with a syringe. The receiving aperature 50 of one or more embodiments of the tray 40 may have a cross-sectional shape that is compatible with a cross-sectional shape of the needle hub or needle shield. In one variant, the inlet of the tray, the needle hub and/or needle shield may have a non-circular cross-sectional shape.

In one or more embodiments of the present disclosure, the receiving aperture 50 that houses one or more needle hubs or needle shields 20 in the tray 40 may include a keying or locking feature. The keying or locking feature on the tray 40 ensures that the needle hubs or needle shields 20 do not rotate while being attached to a syringe.

In one or more embodiments, the needles may be shielded with a needle shield and the keying or locking feature of the tray would ensure that the needle shield does not rotate while the needle is being attached to a syringe. In one or more embodiments, the needles may be unshielded and the keying or locking feature of the tray would ensure that the needle hub does not rotate while the needle is being attached to a syringe. An advantage of the embodiments of the present disclosure over known packaging solutions is that the locking mechanism is used to hold the needle hubs and/or shields in place. This enables a positive engagement between the syringe and the needle hub or needle shield to allow for single handed techniques.

As used in this specification and the appended claims, the term "irregularly shaped" means that the cross-sectional shape provides a surface or edge that is detrimental to free rotation about the cross-section. For example, a hexagon or oval shape would be considered "irregular". A receiving aperature with an irregular inner surface may contain and prevent rotation of the needle hub or a needle shield relative to the tray. In one or more embodiments, the needle hub or a needle shield is irregularly shaped to prevent rotation of the needle hub or needle shield relative to the receiving aperture. For example, the needle hub or a needle shield may have a hexagonal shape matching a hexagonal shaped receiving aperature. The receiving aperture is sized and shaped to receive a needle hub or a needle shield. The cross-sectional shape of the opening of the receiving aperture of the tray can be any suitable symmetric or non-symmetric polygonal shape including, but not limited to, triangular, square, pentagonal, hexagonal, heptagonal, octagonal, and cruciform. In some embodiments, the receiving aperture is irregularly shaped. For example, a hexagon or oval shape would be considered "irregular". Similarly, the cross-sectional shape of the corresponding needle hub or a needle shield can be any suitable symmetric or non-symmetric polygonal shape including, but not limited to, triangular, square, pentagonal, hexagonal, heptagonal, octagonal, rectangular, and cruciform. In some embodiments, the needle hub or a needle shield is irregularly shaped.

As shown in FIGS. 3-6, the cross-sectional shape of the opening of the receiving aperture 50 of the tray 40 includes a distally extending side wall 51 having a square, cruciform, triangular or hexagonal cross-section and a connecting section between the distally extending wall 51. The square, cruciform, triangular or hexagonal cross-section of the distally extending wall 51 is compatible with a needle hub or needle shield 20 having a corresponding square, cruciform, triangular or hexagonal cross-section, which is prevents rotation of rotation of the needle hub or needle shield 20 when the needle hub or needle shield is being connected with a syringe.

As shown in FIG. 3, in an alternative embodiment, the cross-sectional shape of the opening of the receiving aperture 50 of the tray 40 has a square cross-section and includes four walls each having two side edges each, wherein all four walls are joined by at least two side edges to each other to form a hollow square configuration having four sides that surrounds a needle hub or needle shield. The needle hub or needle shield includes a corresponding square cross-section having four walls each having a side edge, wherein all four walls are joined at least two side edges each other to form a hollow square configuration having four sides that form a inlet cavity having a square cross-section.

Figure 5:
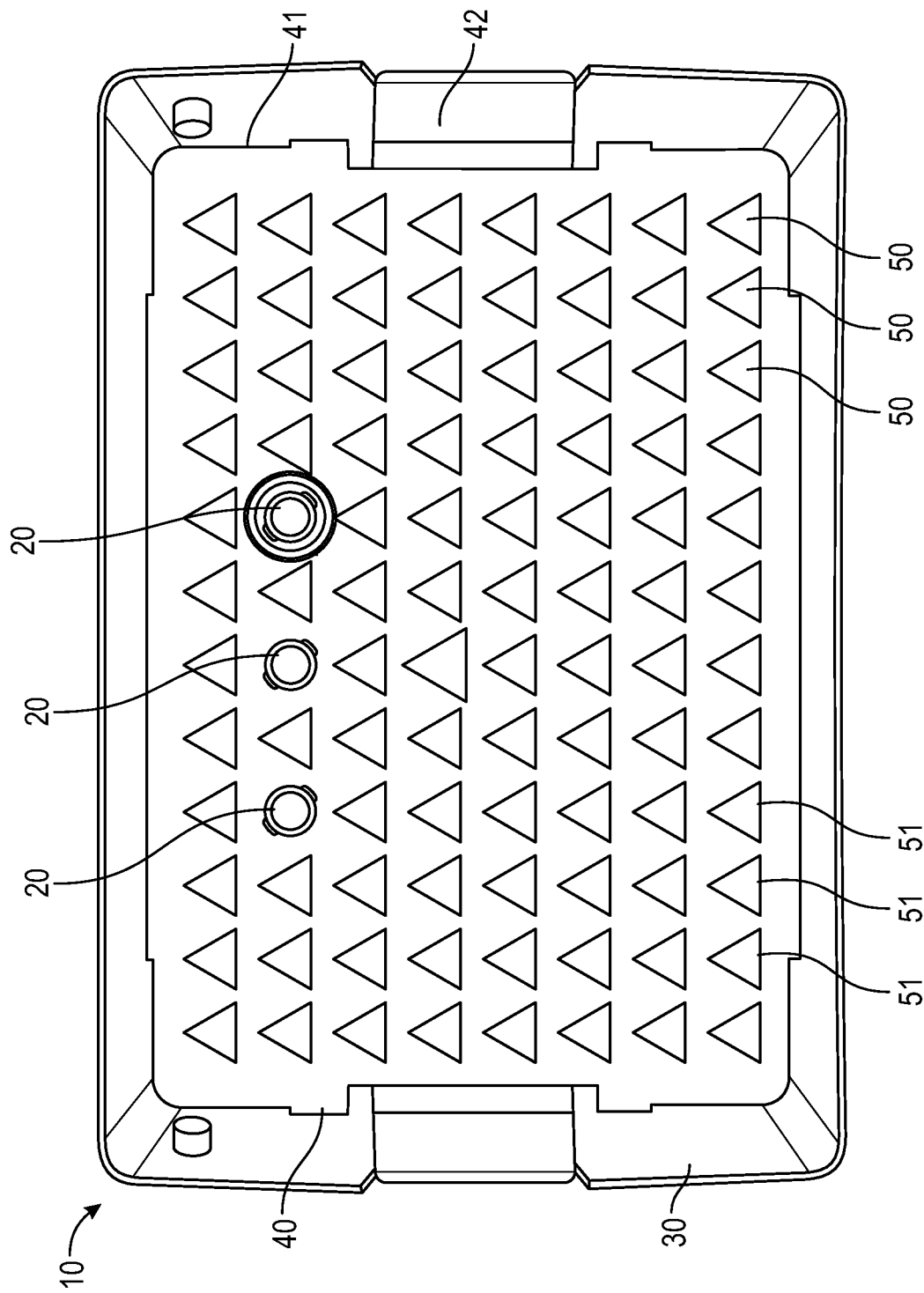
FIG. 5 illustrates a top view of a container and tray having a representative triangle-shaped locking feature for a needle hub or needle shield of the needle packaging with a few representative needles illustrated according to an embodiment.
Figure 6:
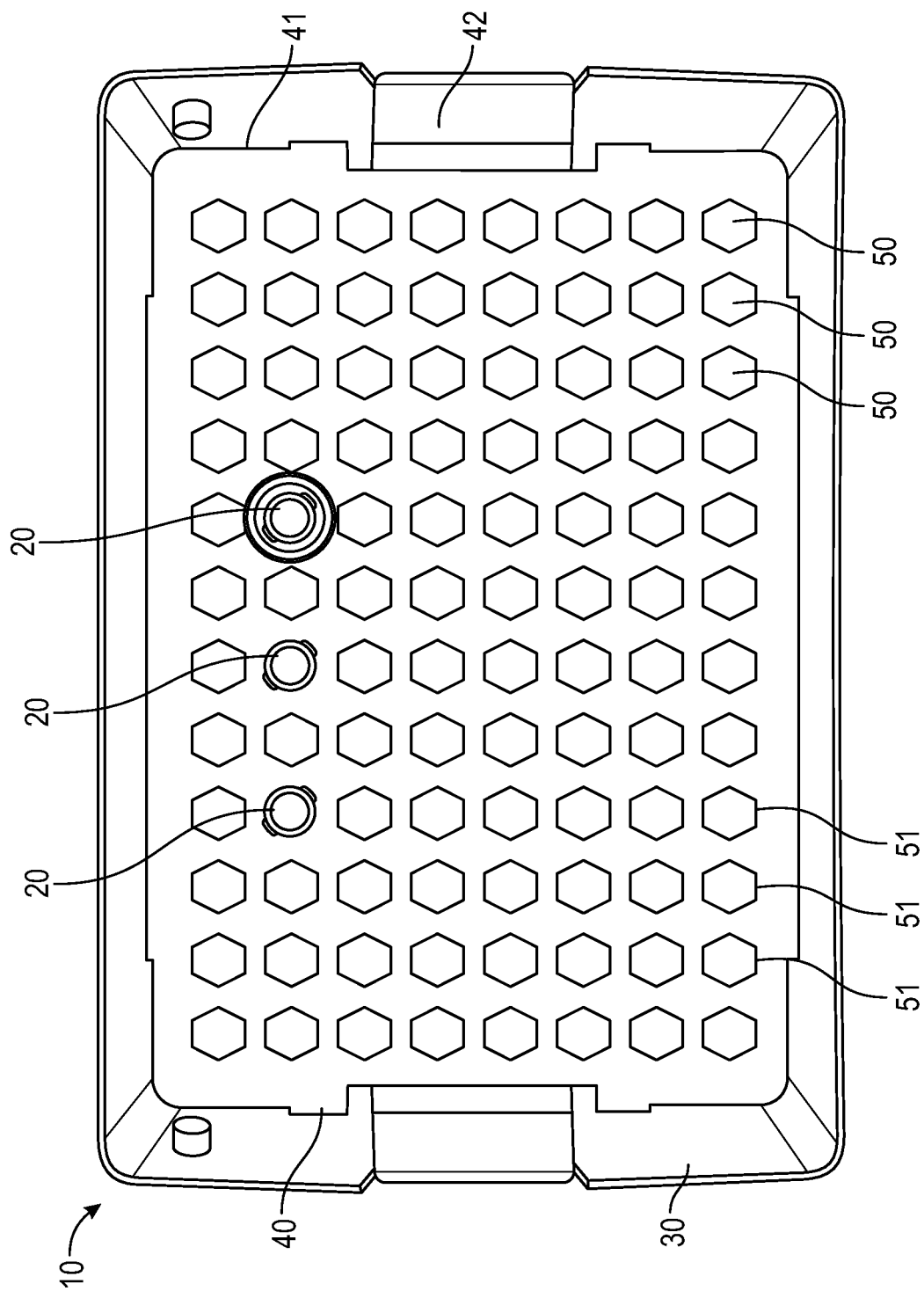
FIG. 6 illustrates a top view of a container and tray having a representative hexagonal-shaped locking feature for a needle hub or needle shield of the needle packaging with a few representative needles illustrated according to an embodiment.

As shown in FIG. 5, in an alternative embodiment, the cross-sectional shape of the opening of the receiving aperture 50 of the tray 40 has a triangular cross-section. The opening of the tray includes three walls, each having two side edges each, wherein all three walls are joined by at least two side edges to each other to form a hollow triangular configuration having three sides that surround a corresponding needle hub or needle shield.

In one or more embodiments, the lid 60 lies flush with the top wall of the container 30 and overlies the needle hubs or needle shield containing the needle disposed within the receiving apertures 50 of the tray to prevent the contamination of the needles, needle hubs and needle shields disposed in separate receiving apertures 50.

In some embodiments the package 10 also comprises a lid 60 which is either hinged to or lifts off the container. The lid 60 comprising lid sidewalls, a lid proximal surface and a lid interior distal surface. In some embodiments, as shown in FIG. 1, lid 60 comprises four lid sidewalls arranged in a substantially rectangular or square configuration.

The package 10 can be sealed in a variety of ways including, but not limited to, heat-sealing or torturous path closure. In one or more embodiments, the entire tray or container of needles would be guaranteed to be sterile until the package 10 is opened by using a full sterile barrier system or through the use of torturous path closures in the lid, body of the container, or both.

Heat sealing can be performed with uniform thermoplastic monolayers or with materials having several layers, at least one being thermoplastic whereby one thermoplastic layer is sealed or welded to another similar thermoplastic layer using heat and pressure. In one or more embodiments, a layer of protective film is applied over and attached to the entirety or portions of the container to ensure sterility of each of the needles, needle hubs and needle shields disposed within the receiving aperture until the needle is used.

In one or more embodiments, heat sealing can also be made with a substrate or material that allows for a clean peel or cohesive peel mechanism between a lid stock and the base or flange of the tray. This is may be accomplished with a coating applied to a paper or Tyvek material that seals with heat and pressure.

Torturous path closure utilizes a torturous path to prevent the ingress of microorganisms but allows gas, air, and steam to enter and exit the package 10 without compromising sterility. The body of the container or the lid may include an interior surface having a plurality of tortuous path rings or alternating channels. The tortuous path rings create a barrier between the contaminated exterior and the sterile interior region of the needle by creating a long pathway with a plurality of interruptions that prevents the migration of microorganisms from the outside of the needle into the sterile fluid path.

The package 10 may be sealed, or specifically heat-sealed, in a material made from plastic film, aluminum, medical grade papers or Tyvek® that are breathable and permeable to gases for sterilization but are impermeable to microorganisms. The sealing material may be in the form of a film. Tyvek® may be used as a sealing material. Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly breathable, but, at the same time, the material is impermeable to liquid water and microorganisms.

In one or more embodiment, the package 10 of the present disclosure may be manufactured in accordance with an injection molding or thermoform techniques of a character well understood by those skilled in the art.

The container, lid and tray may be formed by standard forming methods known in the art, e.g., by blown film extrusion, cast film extrusion, injection or blow molding, pelletizing, foaming, thermoforming, compounding in polymer melt form, or fiber spinning.

The package 10 can be created via thermoforming. In the case of thermoforming, a plastic sheet is unwound from a reel and guided through a pre-heating station. The temperature of the pre-heating plates is such that the plastic will soften and become pliable. The warm plastic then arrives in a forming station where a large pressure and/or physical pushing with a plug assist forms the container, lid or tray into a negative mold. The mold is cooled such that the plastic becomes firm again and maintains its shape when removed from the mold. The container can comprise plastic such as flexible thermoformable plastics, including, but not limited to, polyethylene, polypropylene, nylon and ethyl vinyl acetate (EVA). The container may also be a multi-layer structures that are made of multiple plastics, including, but not limited to, polyethylene, polypropylene, nylon and ethyl vinyl acetate (EVA). In one or more embodiments, the lid can comprise plastic such as flexible thermoformable plastics, including, but not limited to, polyethylene, polypropylene, nylon and ethyl vinyl acetate (EVA). The lid may also be a multi-layer structures that are made of multiple plastics, including, but not limited to, polyethylene, polypropylene, nylon and ethyl vinyl acetate (EVA). In one or more embodiments, the lid can comprise plastic such as flexible non-thermoformable plastics. The tray can comprise plastic such as flexible thermoformable plastics, including, but not limited to, polyethylene, polypropylene, nylon and ethyl vinyl acetate (EVA). The use of a thermoformed tray or container with a lid to create a sterile barrier would also reduce cost compared to current injection molded trays and containers.

Figure 7:
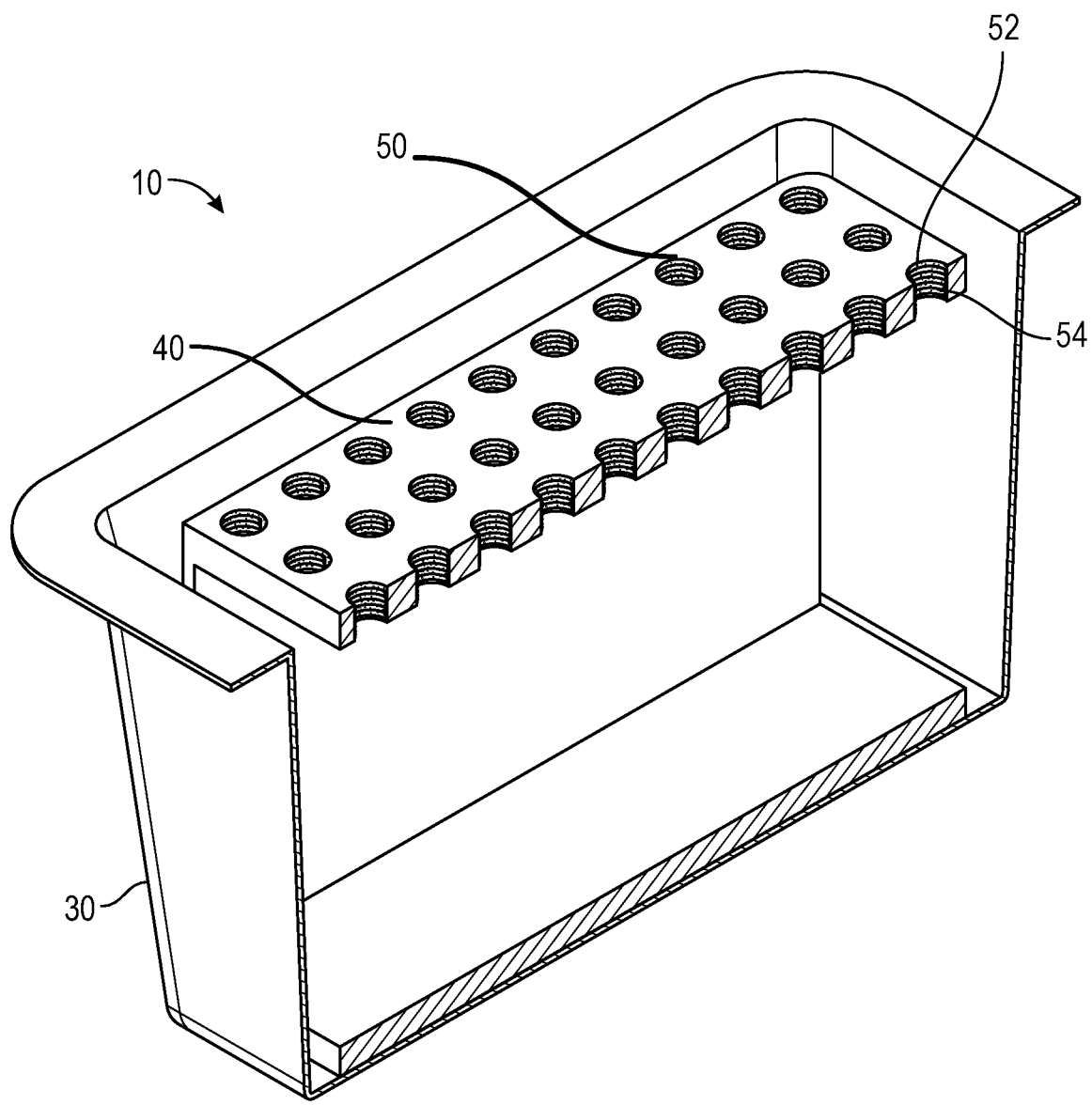
FIG. 7 illustrates a cross-sectional view of a plurality of receiving apertures having a friction enhancing material disposed the plurality of receiving apertures.

In one or more embodiments, friction enhancing surface treatments, coatings, or texture patterns in the plurality of receiving apertures may be used to help prevent rotation during the engagement process of a needle hub or needle shield with a syringe. As shown in FIG. 7, another aspect of the present disclosure relates to a package 10 of sterile needles having a container 30, a tray 40 having a plurality of receiving apertures 50 spaced apart such that the receiving apertures 50 are sized and shaped to receive a needle hub or a needle shield or a plurality of needles within the plurality of receiving apertures 50, a friction enhancing material 54 disposed within the plurality of receiving apertures. In one or more embodiments, a lid, such as lid 60 shown in FIG. 1, may be supported by the container. The lid and container form an enclosure for the plurality of needles.

In one or more embodiments The inside surface of the sidewall 52 of the receiving apertures 50 may be coated or covered with a friction enhancing material 54. In one or more embodiments, the friction enhancing material 54 has an adequate coefficient of friction when in contact with the needle hub or needle shield. In one or more embodiments, the friction enhancing material 54 may be in the form of an inlay set within the sidewall 52 of the receiving aperture 50. In one or more embodiments, the inside surface of the sidewall 52 of receiving apertures may also include high friction contact surface that results in a grippy, tacky or sticky contact between the receiving apertures 50 and the corresponding needle hub or needle shield. The material of construction of the high friction contact surface can be any resilient, flexible material with adequate coefficient of friction with the skin. Suitable friction enhancing materials 54 include substances such as rubber, latex rubber, butyl rubber, silicone, and the like. In one or more alternate embodiment, a friction enhancing texture may be molded into the surface of the plurality of receiving apertures. The friction enhancing texture may be in the form of a knurl pattern or surface treatment on the surface of the plurality of receiving apertures.

Figure 8A:
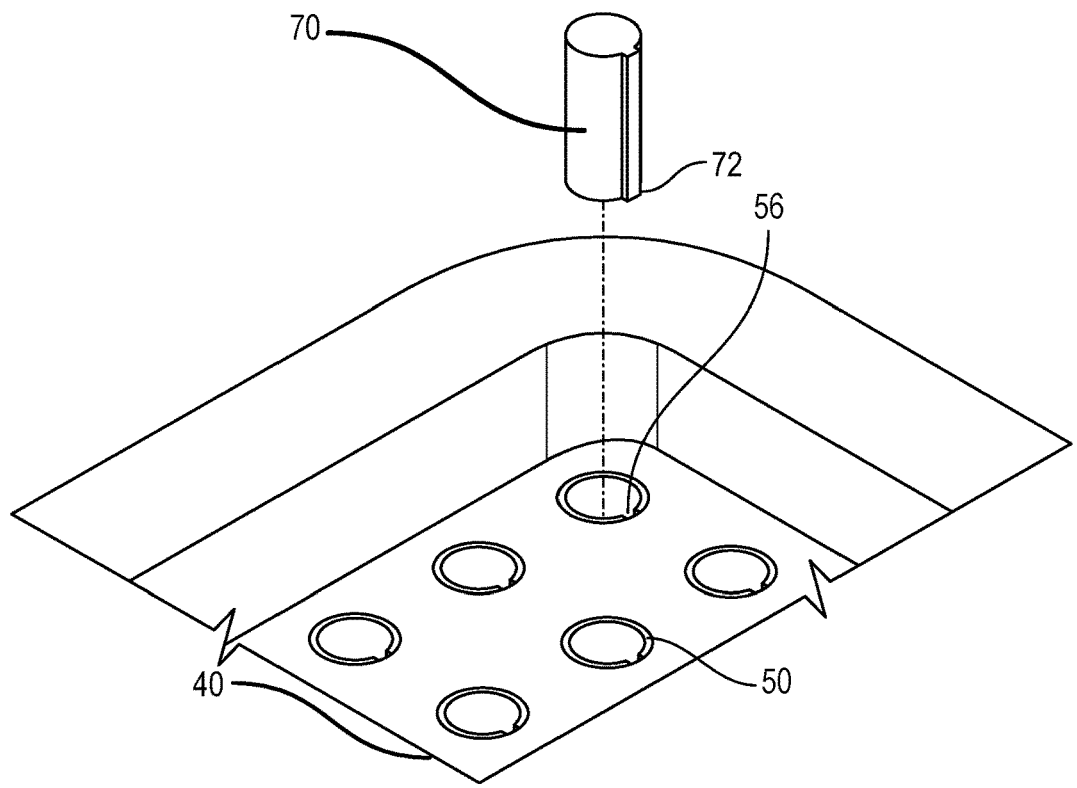
FIG. 8A illustrates a partial top view of a tray having a having a plurality of receiving apertures having a groove that extends partially or fully along the inside surface of the receiving aperture and a needle hub or needle shield having a projection that corresponds to the groove of the receiving aperture.

As shown in FIG. 8A, in one or more alternate embodiment, the receiving aperture of the tray may contain a groove or recess that can extend partially or fully along the inside surface of the receiving aperture while the needle hub or needle shield includes a corresponding projection on its outer surface.

As shown in FIG. 8A, tray 40 includes a plurality of receiving apertures 50, wherein each receiving aperture includes one or more grooves 56 that extends partially or fully along the inside surface of the receiving aperture and a needle hub or needle shield having a projection 72 that corresponds to the groove of the receiving aperture.

As shown in FIG. 8A, to control the rotational movement of the needle hub or needle shield 70 relative to the tray 40, the inside surface of the receiving apertures may include one or more stops or grooves 56 that interact with a corresponding projection 72 on the outer face of the needle hub or needle shield 70 wherein the projection 72 on the outer surface of the needle hub or needle shield rests against the stops or grooves 56 on the inside surface of the receiving aperture 50 to prevent rotation. The stops or grooves 56 provide additional interference to prevent rotation of the needle hub or needle shield to enable a positive engagement between the syringe and the needle hub or needle shield to allow for single handed operation techniques.

Figure 8B:
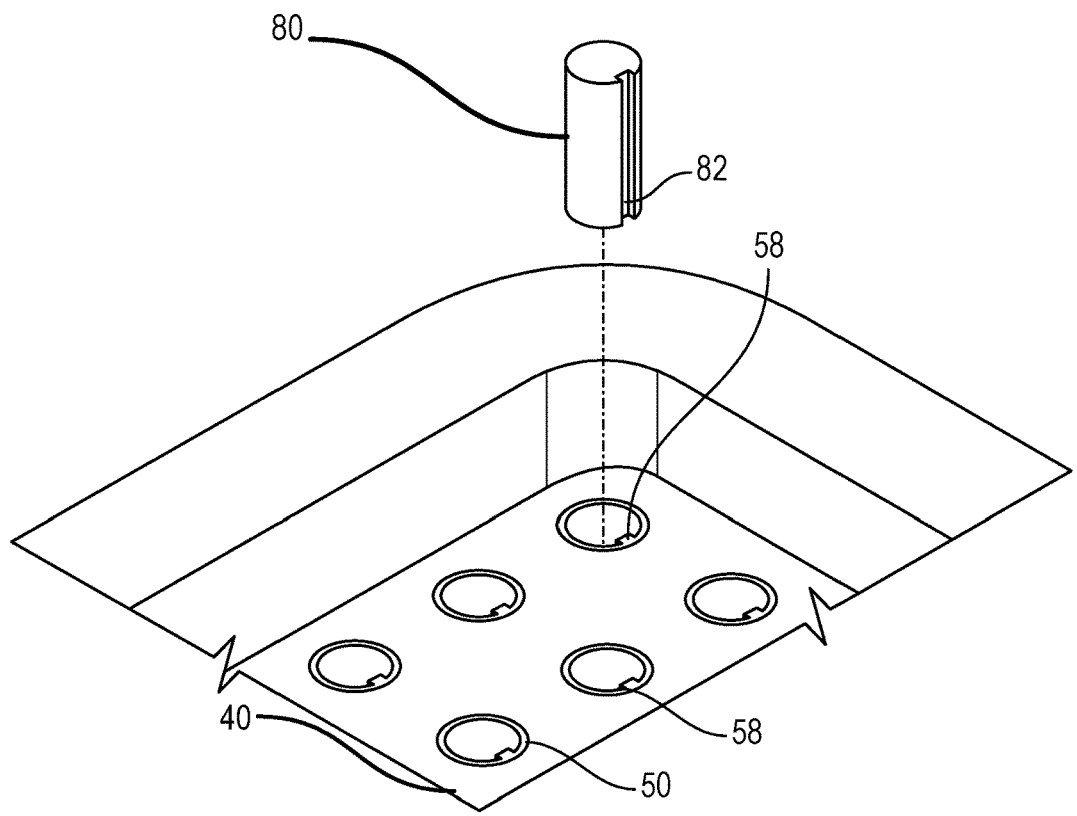
FIG. 8B illustrates a partial top view of a tray having a plurality of receiving apertures having a projection that extends partially or fully along the inside surface of the receiving aperture and a corresponding needle hub or needle shield having a groove to receive the projection of the receiving aperture.

As shown in FIG. 8B, tray 40 includes a plurality of receiving apertures 50 having a projection 58 that extends partially or fully along the inside surface of the receiving aperture and a corresponding needle hub or needle shield 80 having a groove 82 to receive the projection of 58 the receiving aperture 50. As shown in FIG. 8B, to control the rotational movement of the needle hub or needle shield 80 relative to the tray 40, the receiving aperture 50 of the tray 40 may contain a projection 58 that can extend partially or fully along the inside surface of the receiving aperture 50. In one or more embodiments, the projection 58 can extend along any portion of the length of the inside surface of the receiving aperture 50. The projection 58 can start and stop at any point along the length of the inside surface of the receiving aperture 50. The projection 58 can be sized to engage with a corresponding groove 82 or recess on the outer surface of a needle hub or needle shield 80 to facilitate alignment of the needle hub or needle shield 80 with the receiving aperture 50. In one or more alternate embodiments, the groove or recess 82 can extend along any portion of the length of the outer surface of a needle hub or needle shield 80. The groove or recess 82 can start and stop at any point along the length of the outer surface of a needle hub or needle shield 80. The groove or recess 82 can be sized to engage with a corresponding projection 58 on the inside surface of the receiving aperture 50 to facilitate alignment of the needle hub or needle shield 80 with the receiving aperture 50.

In one or more embodiments, the outer face of the needle hub or needle shield 70 may include one or more stops or grooves 56 that interact with a corresponding feature (e.g. ledge) on the inside surface of the receiving apertures wherein the outer feature on the outer surface of the needle hub or needle shield rests against the stop on the inside surface of the receiving aperture to prevent rotation.

Reference throughout this specification to "one embodiment," "certain embodiments," "one or more embodiments" or "an embodiment" means that a particular feature, structure, material, or characteristic described in connection with the embodiment is included in at least one embodiment of the present disclosure. Thus, the appearances of the phrases such as "in one or more embodiments," "in certain embodiments," "in one embodiment" or "in an embodiment" in various places throughout this specification are not necessarily referring to the same embodiment of the present disclosure. Furthermore, the particular features, structures, materials, or characteristics may be combined in any suitable manner in one or more embodiments.

Although the present disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the embodiments of the present disclosure. Thus, it is intended that the present disclosure include modifications and variations that are within the scope of the appended claims and their equivalents.

What is claimed is:

1. A package of sterile needles comprising:
a container having a body including a bottom portion and a side portion connected to and extending from the bottom portion;
a tray having a plurality of receiving apertures spaced apart, the plurality of receiving apertures having a non-circular cross-sectional shape, the plurality of receiving apertures sized and shaped to receive a needle hub or a needle shield, wherein the needle hub is shielded or unshielded, the plurality of receiving apertures having sidewalls defined by a depth of the plurality of receiving apertures, the depth being sufficient to hold the needle hub or the needle shield such that a sidewall of the needle shield or a sidewall of the unshielded needle hub are supported by the sidewalls of the plurality of receiving apertures; and
a plurality of needles disposed within the plurality of receiving apertures, wherein the plurality of needles comprises at least one of the needle hub or the needle shield; and
a lid being supported by said container, said lid and said container forming an enclosure for the plurality of needles; wherein the cross-sectional shape of the plurality of receiving apertures is compatible with a cross-sectional shape of the needle hub or needle shield, wherein rotation of the needle hub or needle shield is prevented when the sidewalls of the plurality of receiving apertures are in contact with the sidewall of the needle shield or the sidewall of the unshielded needle hub;
wherein the cross-sectional shape of the plurality of receiving apertures have at least one of a cruciform shape, a square shape, a rectangular shape or a triangular shape, wherein the cross-sectional shape of the needle hub or needle shield have at least one of a cruciform shape, a square shape, a rectangular shape or a triangular shape.

2. A package of sterile needles comprising:
a container having a body including a bottom portion and a side portion connected to and extending from the bottom portion;
a tray having a plurality of receiving apertures spaced apart, the plurality of receiving apertures having a non-circular cross-sectional shape, the plurality of receiving apertures sized and shaped to receive a needle hub or a needle shield;
a friction enhancing material disposed in the plurality of receiving apertures;
a plurality of needles disposed with the plurality of receiving apertures; wherein the plurality of needles comprises at least one of the needle hub or the needle shield, wherein the needle hub is shielded or unshielded; and
a lid being supported by said container, said lid and said container forming an enclosure for the one or more needle hub or needle shield; wherein the plurality of receiving apertures having sidewalls defined by a depth of the plurality of receiving apertures, the depth being sufficient to hold the needle hub or the needle shield such that that a sidewall of the needle shield or a sidewall of the unshielded needle hub are supported by the sidewalls of the plurality of receiving apertures;
wherein the cross-sectional shape of the plurality of receiving apertures is compatible with a cross-sectional shape of the needle hub or needle shield, wherein rotation of the needle hub or needle shield is prevented when the sidewalls of the plurality of receiving apertures are in contact with the sidewall of the needle shield or the sidewall of the unshielded needle hub;
wherein the cross-sectional shape of the plurality of receiving apertures have at least one of a cruciform shape, a square shape, a rectangular shape or a triangular shape, wherein the cross-sectional shape of the needle hub or needle shield have at least one of a cruciform shape, a square shape, a rectangular shape or a triangular shape.

3. The package of claim 2, wherein the friction enhancing material is rubber.

4. The package of claim 2, wherein the friction enhancing material is silicone.

* * * * *